US00PP27659P3

(12) United States Plant Patent
Cranwell

(10) Patent No.: US PP27,659 P3
(45) Date of Patent: Feb. 14, 2017

(54) APPLE TREE NAMED 'TCL3'

(50) Latin Name: *Malus domestica*
Varietal Denomination: TCL3

(71) Applicant: David F. Cranwell, Havelock North (NZ)

(72) Inventor: David F. Cranwell, Havelock North (NZ)

(73) Assignee: Te Mata Consultants Limited (NZ)

( * ) Notice: Subject to any disclaimer, the term of this patent is extended or adjusted under 35 U.S.C. 154(b) by 243 days.

(21) Appl. No.: 14/121,707

(22) Filed: Oct. 9, 2014

(65) Prior Publication Data

US 2016/0106014 P1 Apr. 14, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell
(74) *Attorney, Agent, or Firm* — Randall Danskin P.S.

(57) ABSTRACT

A new and distinct variety of apple tree is described and which is distinguished as to novelty by producing an attractively colored apple which is ripe for harvesting and shipment on and about the last week of January under the ecological conditions prevailing near Havelock North, New Zealand.

3 Drawing Sheets

Latin name: *Malus Domestica.*
Varietal denomination: TCL3.

BACKGROUND OF THE NEW VARIETY

The present invention relates to a new, novel, and distinct variety of apple tree which has been denominated varietally as 'TCL3', and more specifically to a novel apple tree which produces fruit which are ripe for harvesting and shipment beginning the last week of January under the ecological conditions which are prevailing in the Inventor's orchard which is located near River Road, Havelock North, New Zealand.

ORIGIN AND ASEXUAL REPRODUCTION

It has long been recognized that an important factor contributing to the success of any new variety of apple tree bearing fruit for the fresh market is it's relative date of harvesting in comparison to other varieties bearing similar fruit in the same season. Further, another significant factor affecting the commercial viability of a new variety of apple tree relates to the appearance of the fruit it produces, as well as its fruit size, and its ability to be held for commercially acceptable periods of time in cold storage.

The new variety of apple tree as described hereinafter was derived by the following methodology. The new variety was selected from a population of seedlings which were earlier derived from crossing the apple tree varieties 'Sciros' (U.S. Plant Pat. No. 7,814) with the apple tree variety 'Tenroy' (U.S. Plant Pat. No. 4,121) during the 2001 growing season. The crossing of these two patented varieties were made by the Inventor of record at his orchard which is located near River Road, Havelock North, New Zealand. Fruit from these first crosses were first evaluated in 2005. The new and promising variety was then selected for further asexual propagation in the same season. These new second generation trees were propagated by budding onto 'M26' rootstock (unpatented) at a commercial nursery which is located in Hastings, NZ. The second generation trees were then planted in the aforementioned orchard of the Inventor. Fruit produced from the second generation trees have been subsequently evaluated and compared and contrasted against the original seedling which was evaluated in 2005. The Inventor has confirmed that the fruit produced by these subsequent asexually reproduced trees, and the other botanical characteristics which were earlier observed are the same as that seen in the original promising seedling that was first identified during the 2005 growing season.

SUMMARY OF THE VARIETY

The new and novel tree which is described hereinafter characterized as to novelty by producing an attractively colored fruit which is ripe for harvest and shipment beginning the last week of January under the ecological conditions prevailing near Havelock North, New Zealand. This date of harvesting is relatively early when compared with the harvest time of the 'Sciros' apple tree, (U.S. Plant Pat. No. 7,814) and which is harvested at the beginning of April under the ecological conditions prevailing in New Zealand. Further, the present variety of apple tree is distinguishable from the variety 'Tenroy' (U.S. Plant Pat. No. 4,121) which produces fruit having a pattern of over color which is striped, whereas the present new variety of apple tree produces fruit which has a blushed coloration. Still further in relative comparison to the variety 'Sciearly' (unpatented) and which is probably one of the closest known varieties, the fruit produced by 'Sciearly' produces fruit having an over-color which is considered red, (RHS 46A), whereas the over color as seen on the fruit produced by the new variety is pink (RHS 48A).

BRIEF DESCRIPTION OF THE DRAWINGS

The accompanying drawings are color photographs of the present variety.

NOT A COMMERCIAL WARRANTY

Figure 1:
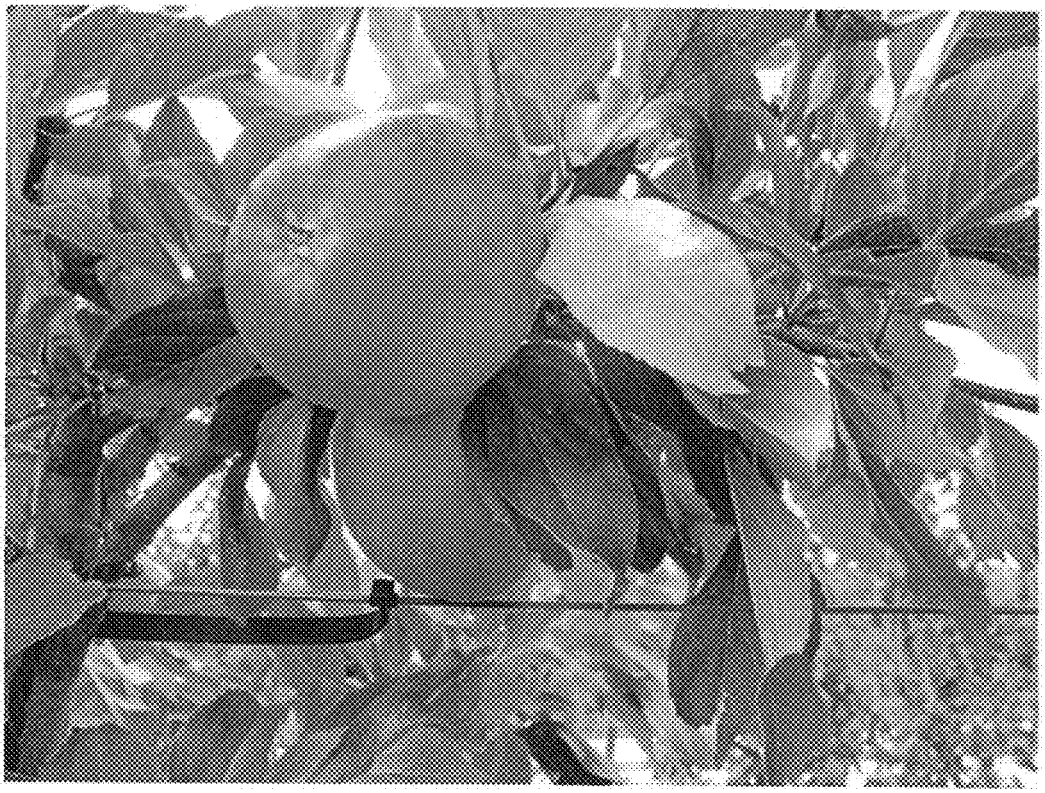
FIG. 1 depicts the current growing habit of the new variety of apple tree. The photograph depicts several fruit which are sufficiently ripe for harvesting and shipment.
Figure 2:
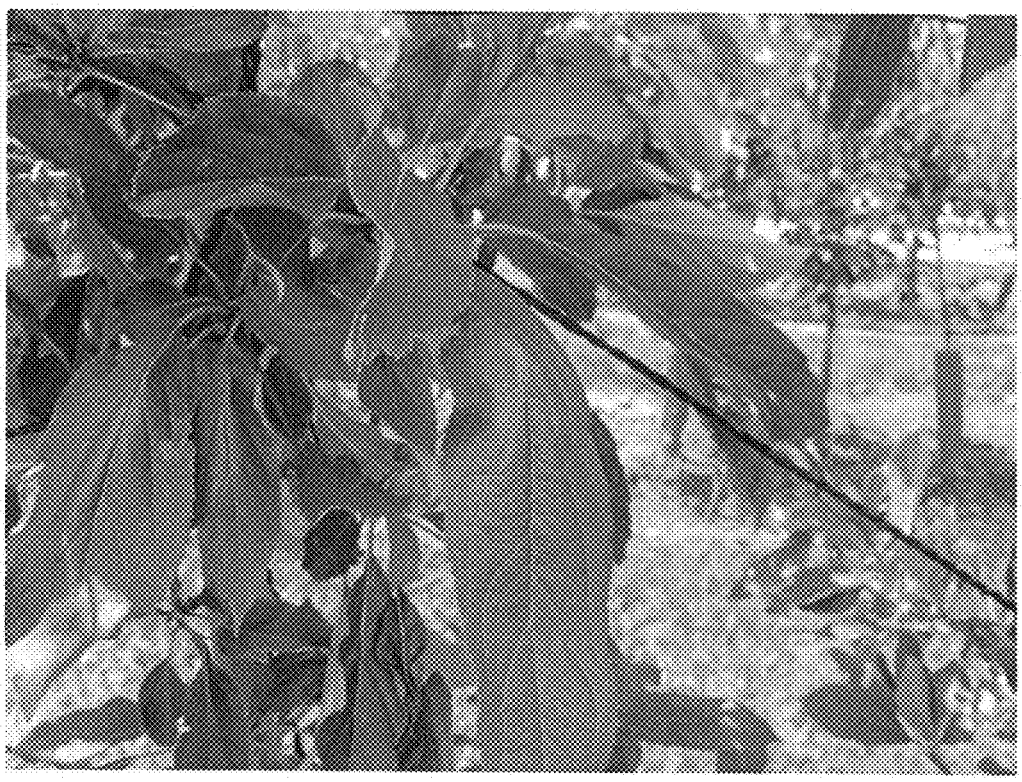
FIG. 2 depicts the leaf growth habit of the new variety of apple tree.
Figure 3:
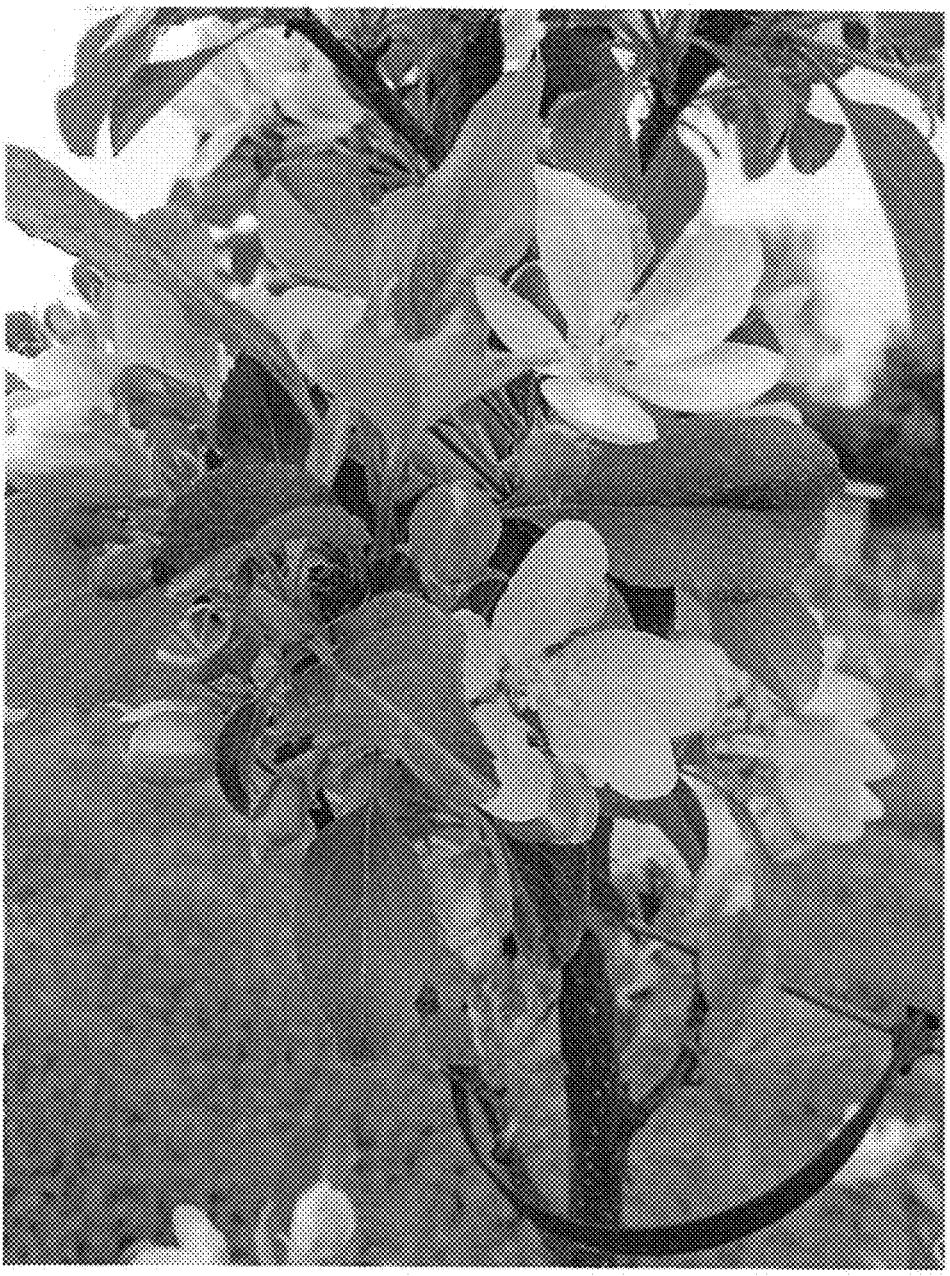
FIG. 3 depicts the flowering characteristics of the new apple tree.

The following detailed description has been prepared to solely comply with the provisions of 35 U.S.C. §112, and does not constitute a commercial warranty (either expressed or implied) that the present variety of apple tree will, in the future, display all of the botanical, pomological or other growth characteristics as set forth, hereafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of apple tree, the following has been observed during the 2014 growing season under the ecological conditions prevails in the orchard of the Inventor which is located near Havelock North, New Zealand. All major color code designations are by reference to The R.H.S. Colour Chart (1995), and which is provided by The Royal Horticultural Society of Great Britain.

TREE

*Tree vigor.*—Considered average for the species.

*Tree type.*—Ramified.

*Growth habit.*—Generally — Considered spreading.

*Tree size.*—At the time of observation during the 2014 growing season, the second generation trees, which are about 5 years old, were about 2 meters in height, and about 1 meter in width.

TRUNK

Trunk size: Generally — On the observed trees, noted above, the trunk diameter was about 31 mm when measured at a distance of about 15 cm above the graft union.

Bark: Generally — The surface texture of the bark is generally smooth and has a gray color (RHS 201D).

Trunk lenticels: Generally — Considered moderate in number. Typically 4 lenticels per square cm of bark surface area are observed.

Lenticel size: About 2 mm in length and about 1 mm in width.

*Lenticel color.*—Gray-white (RHS 156D).

Branches:

*Average branch sizes.*—Approximately 50 cm long when measured at a distance of about 1.2 meters above the surface of the earth.

*Branch diameter.*—About 15 mm when measured at a distance of about 25 cm from the trunk.

*Crotch angle.*—The crotch angle may vary between about 0° to about 30° when measured from the horizontal plain.

*Branch color.*—Gray-orange (RHS 177B).

*Dormant one year old shoots.*—Length — About 180 mm. Dormant 1 year old shoots — diameter — about 4 mm. Shoot Texture — Smooth.

*Pubescence.*—Absent.

*Dormant one year old shoots.*—Color — Gray-orange, (RHS 166A).

*Dormant one year old shoots.*—Internode length — About 29 mm.

*Dormant one year old shoots.*—Lenticels — Generally speaking the lenticels are moderate in number. Usually, 18 lenticels per square cm of bark surface area is observed.

*Lenticels.*—Size — About 0.6 mm in diameter.

*Lenticels.*—Color — Gray-white (RHS 156D).

*Spur diameter.*—About 4 mm.

*Spur length.*—About 14 mm.

*Spur distance.*—The distance between each spur is irregular and not able to be reasonably measured.

FLOWERS

*Flower buds.*—Numbers — 1 per spur is typically observed.

*Flower buds.*—Shape — Pointed.

*Flowers buds.*—Length — About 10 mm.

*Flower buds.*—Diameter — About 4 mm.

*Flower height.*—As measured from the base of the petals to the top of the stamens this distance is about 18 mm. The flower height when fully open is about 51 mm.

*Flower buds.*—Color — Gray-orange (RHS 166A).

*Flower color.*—Generally speaking at the balloon stage, the flower color is red, (RHS 45D).

*Flower size.*—Generally considered to be medium for the species.

*Flower fragrance.*—Weak and typical of apple tree blossoms.

*Flower petals.*—Numbers — 5 petals per flower is observed.

*Petal margins.*—Considered overlapping.

*Petal shape.*—The petals have a rounded apex, and a smooth margin.

*Petal color.*—Upper surface — Red-purple (RHS 69D) and having a blush of red (RHS 54B).

*Petals.*—Color — Lower surface — red-purple (RHS 69B).

*Petal length.*—About 23 mm.

*Petal width.*—About 15 mm.

*Petal base shape.*—Indistinguishable for other apple tree blossoms.

*Sepals.*—Numbers — 5 per flower are typically observed.

*Sepals.*—Shape — Pointed.

*Sepals.*—Color — The dorsal and ventral surfaces of the respective sepals each have a color of RHS 139C.

*Sepal marginal form.*—Considered smooth and hirsute.

*Stamens.*—Numbers — Typically more than 15 stamens are observed.

*Filaments.*—Length — About 7 mm.

*Style size.*—About 10 mm. in length, and less than 1 mm. in diameter.

*Filaments.*—Color — Green-yellow (RHS 1C).
*Stamen length.*—On average about 13 mm.
*Anthers.*—Shape — Kidney like.
*Anthers.*—Color — Yellow (RHS 8C).
*Anther length.*—About 2 mm.
*Pistil.*—Length — About 7 mm.
*Pistil number per flower.*—Typically 5.
*Stigma.*—Color — Yellow-orange (RHS 16D).
*Stigma shape and size.*—Oval and bulbous and having a length dimension of about 2 mm.; and a diameter of about 0.8 mm.
*Style color.*—Yellow-green, (RHS 150D).
*Ovary color.*—Yellow-green (RHS 150D).
*Ovary length.*—About 3 mm.
*Time of flowering.*—Generally — Considered early. Full bloom is observed under the ecological conditions prevailing in Havelock North, New Zealand on the 8th of October during typical growing seasons.
*Pollen color.*—Yellow (RHS 8C).
*Pollination.*—Generally — Any diploid variety which flowers at approximately the same season will serve as a pollinizer for the new variety of apple tree.
*Blooming period.*—In Havelock NZ, about October 2-14 under typical ecological conditions.

LEAF

*Leaf attitude.*—Generally speaking, the leaf faces upwardly in relation to the shoot.
*Leaf length.*—About 9 cm.
*Leaf width.*—About 4.2 cm.
*Leaf base shape.*—Acuminate.
*Ratio of leaf length to leaf width.*—Considered average for the species.
*Leaf shape.*—Elliptical and having a pointed tip.
*Leaf margin.*—Considered biserrate.
*Leaf color.*—Upper Surface — Green (RHS 139A).
*Leaf color.*—Lower Surface — Yellow-green (RHS 148C).
*Leaf petiole length.*—Considered average, about 2.8 cm.
*Leaf petiole diameter.*—About 1.5 mm.
*Leaf petiole color.*—Yellow-Green (RHS 145B).
*Leaf pubescence.*—A weak pubescence may be observed on the lower surface of the leaf.
*Leaf stipule size.*—About 8 mm. in length; and about 0.7 mm. in diameter.
*Leaf stipule color.*—Green (RHS 139A).

FRUIT

Fruit size: Considered average for the species.
*Fruit diameter.*—About 75 mm.
*Fruit height.*—About 65 mm.
*Fruit weight.*—On average about 180 grams per fruit.
*Fruit shape.*—Generally considered conical.
*Fruit ribbing.*—Generally considered to be absent.
*Fruit calyx.*—Generally, the calyx is considered to be closed.
*Fruit firmness.*—About 8 kgF when measure with a penetometer having a tip which is about 11 mm. in diameter.
*Calyx diameter.*—About 7 mm.
*Basin diameter.*—About 25 mm.
*Basin depth.*—About 5 mm.
*Stem cavity.*—Diameter — About 33 mm.
*Stem cavity.*—Depth — About 11 mm.
*Fruit lenticels.*—Generally speaking about 8 lenticels per square cm of surface area are evident. However, the lenticels are typically more prominent on the reverse side of the fruit.
Fruit bloom: Absent.
Fruit greasiness: Considered absent.
*Ground color.*—Green-yellow (RHS 1C).
*Over-color.*—75% of the fruit surface has a pink over color (RHS 48A).
*Flesh aroma.*—Mild.
*Eating quality.*—Considered high. The fruit is crips and juicy.
*Brix.*—About 15.5 degrees at harvest maturity.
*Acidity.*—The titratable acidity is about 0.12% at harvest.
*Flush Texture.*—Considered crisp, juicy and sweet.
*Seeds.*—Numbers — 9 seeds per fruit are typically found.
*Locule numbers.*—Typically 5.
*Seeds.*—Shape — Pointed.
*Seeds.*—Size — About 8 mm in length and 4 mm in width.
*Seeds.*—Color — Gray-orange (RHS 176A).
*Fruit harvest time.*—Early for the species, beginning the last week of January under the ecological conditions prevailing in Havelock North, New Zealand. The fruit harvest occurs about 30 January-13 February under typical environmental conditions.
*Storage quality.*—Considered good. No significant disorders for the fruit were evident after the fruit was stored for 100 days in cold storage.
Market use: Considered a fresh dessert fruit for both local and long distant markets.
Disease and insect resistance: The present variety is considered to be susceptible to all insects and diseases found in the region of Havelock North, New Zealand. Although the new variety of apple tree possesses the described characteristics when grown under the ecological conditions prevailing near Havelock North, New Zealand, it should be understood that the variations of the usual magnitude in characteristics incident to changes in growing conditions, fertilization, pruning and pest control as well as horticultural management practices are to be expected.

Having thus described and illustrated my new variety of apple tree what I claim is new and desire to secure by plant Letters Patent is:

1. A new and distinct variety of apple tree as illustrated and described, and which is characteristic principally as to novelty by producing an attractively colored apple which is ripe for harvesting and shipment during the last week in January under the ecological conditions prevailing near Havelock North, New Zealand.

* * * * *